(12) United States Patent
Qiu

(10) Patent No.: US 11,241,548 B2
(45) Date of Patent: Feb. 8, 2022

(54) MOUTHPIECE, AND AUTOMIZING DEVICE COMPRISING THE MOUTHPIECE

(71) Applicant: CHANGZHOU JWEI INTELLIGENT TECHNOLOGY CO., LTD., Changzhou (CN)

(72) Inventor: Weihua Qiu, Changzhou (CN)

(73) Assignee: CHANGZHOU JWEI INTELLIGENT TECHNOLOGY CO., LTD., Changzhou (CN)

( * ) Notice: Subject to any disclaimer, the term of this patent is extended or adjusted under 35 U.S.C. 154(b) by 557 days.

(21) Appl. No.: 15/932,912

(22) Filed: May 18, 2018

(65) Prior Publication Data

US 2018/0263289 A1    Sep. 20, 2018

Related U.S. Application Data

(63) Continuation of application No. PCT/CN2016/104181, filed on Nov. 1, 2016.

(30) Foreign Application Priority Data

Nov. 18, 2015 (CN) .......................... 201510794763.2
Jul. 20, 2016 (CN) .......................... 201620771056.1

(51) Int. Cl.
*A61M 11/04* (2006.01)
*A24F 40/485* (2020.01)
(Continued)

(52) U.S. Cl.
CPC .......... *A61M 11/042* (2014.02); *A24F 40/485* (2020.01); *A24F 40/51* (2020.01);
(Continued)

(58) Field of Classification Search
CPC .... A24F 47/00; A24F 7/00; A24F 7/02; A24F 7/04; A24F 47/008; A24F 40/10;
(Continued)

(56) References Cited

U.S. PATENT DOCUMENTS 4,771,381 A * 9/1988 Norman ............... A24C 5/3406
131/330
4,947,875 A * 8/1990 Brooks ................. A24F 47/006
128/202.21
(Continued)

FOREIGN PATENT DOCUMENTS

CN     103704886 A     4/2014
CN     203762283 U     8/2014
(Continued)

OTHER PUBLICATIONS

"Smoke—Definition of Smoke," Oct. 8, 2020 (Year: 2020).*
(Continued)

*Primary Examiner* — Justine R Yu
*Assistant Examiner* — Benjamin M. Kusiak
(74) *Attorney, Agent, or Firm* — J.C. Patents

(57) ABSTRACT

A mouthpiece and an atomizing device including the mouthpiece are provided, the mouthpiece includes an upper cover body, a sensor assembly and a base, where both the upper cover body and the base are hollow structures which open at both ends; the upper cover body is sleeved on one end of the base; an inner surface of the upper cover body and an inner surface of the base jointly define an inner cavity of the mouthpiece; the sensor assembly is fixed in the inner cavity of the mouthpiece; an air passage gap is formed in the inner cavity of the mouthpiece; and the sensor assembly includes at least one sensor that functions to detect the temperature or humidity or both of the smoke. The mouthpiece can detect the temperature and/or humidity of the smoke in real time.

15 Claims, 8 Drawing Sheets

(51) Int. Cl.
*A24F 40/51* (2020.01)
*A24F 40/60* (2020.01)
*A61M 15/06* (2006.01)
*A24F 40/10* (2020.01)

(52) U.S. Cl.
CPC .............. *A24F 40/60* (2020.01); *A61M 15/06* (2013.01); *A24F 40/10* (2020.01)

(58) Field of Classification Search
CPC ......... A24F 40/51; A24F 40/43; A61M 15/06; A61M 2205/3368; A61M 16/161; A61M 2205/8206; A61M 11/042; A61M 2205/3653; A61M 15/00–0001; A61M 15/0021–0026; A61M 15/0085; A61M 15/0091; G01N 27/223; G01D 11/245
See application file for complete search history.

(56) References Cited

U.S. PATENT DOCUMENTS

| | | | | |
|---|---|---|---|---|
| 2007/0023034 | A1* | 2/2007 | Jongejan | A61M 15/009 128/200.14 |
| 2012/0285236 | A1* | 11/2012 | Haartsen | A61M 15/009 73/204.11 |
| 2013/0087144 | A1* | 4/2013 | Todd | A61M 11/042 128/203.14 |
| 2014/0318557 | A1* | 10/2014 | Bremer | A24F 1/00 131/328 |
| 2014/0345633 | A1* | 11/2014 | Talon | A61M 15/06 131/329 |
| 2015/0020828 | A1* | 1/2015 | Liu | A24F 47/008 131/329 |
| 2015/0090277 | A1* | 4/2015 | Xiang | A24F 47/008 131/328 |
| 2015/0245654 | A1* | 9/2015 | Memari | H02J 50/10 141/2 |
| 2015/0327596 | A1* | 11/2015 | Alarcon | H04L 67/22 131/328 |
| 2016/0007653 | A1* | 1/2016 | Tu | F22B 1/284 392/403 |
| 2016/0057811 | A1* | 2/2016 | Alarcon | A24F 40/50 219/494 |
| 2016/0106153 | A1* | 4/2016 | Zhu | H05B 3/44 131/329 |
| 2016/0128388 | A1* | 5/2016 | Liu | H05B 3/00 392/404 |
| 2016/0338407 | A1* | 11/2016 | Kerdemelidis | H05B 1/0244 |
| 2017/0311648 | A1* | 11/2017 | Gill | A24F 40/465 |
| 2018/0146713 | A1* | 5/2018 | Robinson | H05B 3/42 |

FOREIGN PATENT DOCUMENTS

| | | |
|---|---|---|
| CN | 203872993 U | 10/2014 |
| CN | 104397876 A | 3/2015 |
| CN | 104605481 A | 5/2015 |
| CN | 204483016 U | 7/2015 |
| CN | 204670388 U | 9/2015 |
| CN | 105249539 A | 1/2016 |
| CN | 205180369 U | 4/2016 |
| KR | 10-2012-0051570 A | 5/2012 |
| WO | WO 2015/068044 A2 | 5/2015 |
| WO | WO 2015/128666 A1 | 9/2015 |

OTHER PUBLICATIONS

E+E Elektronik, "EE071 Humidity and Temperature Probe," Mar. 10, 2015. (Year: 2015).*
E+E Elektronik, "EE071 Image," Nov. 1, 2013. (Year: 2013).*
E+E Elektronik, "EE071 User Manual" (Year: 2015).*
The International Search Report of corresponding International PCT application No. PCT/CN2016/104181, dated Dec. 30, 2016.
The Chinese First Search Reports of corresponding China patent application No. 201510794763.2.
The Chinese Second Search Reports of corresponding China patent application No. 201510794763.2.

* cited by examiner

MOUTHPIECE, AND AUTOMIZING DEVICE COMPRISING THE MOUTHPIECE

CROSS-REFERENCE TO RELATED APPLICATIONS

This application is a continuation of International Application No. PCT/CN2016/104181, filed on Nov. 1, 2016, which claims priority to Chinese Patent Application No. 201510794763.2, filed on Nov. 18, 2015, and Chinese Patent Application No. 201620771056.1, filed on Jul. 20, 2016. All of the aforementioned patent applications are hereby incorporated by reference in their entireties.

TECHNICAL FIELD

The disclosure relates to the technical field of electronic cigarettes, in particular to a mouthpiece, and an atomizing device comprising the mouthpiece.

BACKGROUND

At present, electronic cigarettes have become a relatively proven smoking substitute in the market. Generally, an atomizer, or more generally, an atomizing device, is powered by a battery, and driven by electricity, the atomizer heats the smoke liquid to generate smoke, so that the user can experience the smoking.

However, individual users have different needs on the taste of the smoke, and some users may expect a high temperature, dry smoke, while others may expect a lower temperature and humid smoke. Therefore, it is necessary to provide an electronic cigarette that can adjust the smoke temperature or the humidity in real time according to user preferences.

SUMMARY

According to the above technical problem, an objective of the disclosure is to provide a mouthpiece, an atomizing device provided with the mouthpiece, and an electronic cigarette including the atomizing device.

The technical solution to realize above purposes is:

A mouthpiece, including: an upper cover body; a sensor assembly; and a base, where both the upper cover body and the base are hollow structures which open at both ends; the upper cover body is sleeved on one end of the base; an inner surface of the upper cover body and an inner surface of the base jointly define an inner cavity of the mouthpiece; the sensor assembly is fixed in the inner cavity of the mouthpiece; an air passage gap is formed in the inner cavity of the mouthpiece; and the sensor assembly includes at least one sensor that is a temperature sensor or a humidity sensor or a temperature and humidity sensor, which functions to detect the temperature and/or the humidity of smoke flowing through the air passage gap.

Furthermore, the mouthpiece also includes: a protective sleeve that is provided with an accommodating cavity, where the sensor assembly is detachably accommodated in the accommodating cavity, and is fixed in the inner cavity of the mouthpiece together with the protective sleeve; the air passage gap is a gap between the protective sleeve and the inner cavity of the mouthpiece; a through hole connecting the accommodating cavity with the air passage gap is defined in the protective sleeve; and the sensor is provided in the through hole. An atomizer, provided at one end with an aforementioned mouthpiece.

Furthermore, the protective sleeve is provided along a radial direction of the mouthpiece; the accommodating cavity opens along an axial direction of the protective sleeve and extends through the protective sleeve, until forming an open end for the accommodating cavity on an end wall of the protective sleeve; the sensor assembly also includes a PCB (printed circuit board) that is provided on one end with the sensor, and on the other end with an information transmission interface, where the PCB is accommodated in the accommodating cavity and extends along an axial direction of the accommodating cavity, and the information transmission interface is located at the open end of the accommodating cavity; and the upper cover body is provided with a through hole at a position corresponding to the open end of the accommodating cavity.

Furthermore, one side of the base is depressed downward from its top, forming a notch in communication with the through hole; a bottom edge of the notch extends towards the inner cavity of the base, forming a supporting plate; a gap is left between the supporting plate and an inner wall of another side of the base; an end of the supporting plate, which is away from the notch, extends upwards, forming a limiting protrusion, where the notch, the inner wall of the base, the supporting plate and the limiting protrusion jointly define an accommodating groove, and the protective sleeve is at least partially accommodated in the accommodating groove; and the open end of the accommodating cavity faces the notch.

Furthermore, the protective sleeve is provided on its bottom, at a position corresponding to the limiting protrusion, with a stepped groove that abuts against the limiting protrusion; the inner wall of the base is provided with a limiting groove at positions close to both ends of the notch, respectively; and both sides of the protective sleeve are respectively provided with a lower protrusion at positions corresponding to the limiting grooves, where the lower protrusions fit into the corresponding limiting grooves.

Furthermore, a cavity wall of the accommodating cavity is symmetrically provided with two sliding grooves along an axial direction of the accommodating cavity; and two edges of the PCB are provided with two sliding wings engaged with the two sliding grooves, such that, when the PCB is accommodated in the accommodating cavity along the axial direction of the accommodating cavity, the sliding wings are fitted into the corresponding sliding grooves.

Furthermore, the information transmission interface is a USB interface.

Furthermore, the upper cover body is provided on an inner wall of one side with a limiting portion that extends along the radial direction of the upper cover body and is above the through hole; a gap is left between the limiting portion and an inner wall of another side of the upper cover body; and an upper surface of the lower protrusion is provided with an upper protrusion at a position corresponding to the limiting portion, the upper protrusion being provided between the limiting portion and the top end of the base.

Furthermore, the protective sleeve is made of rubber or silica gel.

Furthermore, the base is provided around a periphery of one end opposite to the upper cover body with a groove along a circumferential direction of the base, and a sealing ring is provided in the groove.

An atomizer is provided at one end with any one of the aforementioned mouthpieces.

An electronic cigarette includes a battery device and an aforementioned atomizer.

A mouthpiece, provided in its inner cavity with at least one sensor, where the sensor is a temperature or humidity sensor that functions to detect the temperature or the humidity of the smoke.

Furthermore, the sensors are provided alternatively or symmetrically on both sides of the inner cavity of the mouthpiece, or the sensor is in a circular form, and is circularly provided in the inner cavity of the mouthpiece, or the sensor is provided along, or vertical to, or oblique to, an axial direction of the inner cavity of the mouthpiece.

An atomizing device, including an atomizer, and an aforementioned mouthpiece, wherein the mouthpiece is provided on one end of the atomizer.

An atomizing device includes an aforementioned atomizer, as well as a battery device, where the battery device is connected to another end of the atomizer, functions to power the atomizer, and includes a controller, a storage and a power source, where the atomizer, the storage and the power source are electrically connected with the controller, and the sensor is in signal connection with the controller, where:

the sensor further functions to provide feedback about the detected temperature or humidity of the smoke to the controller;

the controller functions to compare the temperature or the humidity of the smoke with a preset threshold value, and adjust the power output to the atomizer from the power source according to the comparison result;

the storage functions to store the preset threshold value; and the power source functions to supply power to the atomizing device.

Furthermore, when the sensor is a temperature sensor, the storage is reserved with, as a preset threshold value, a preset temperature threshold value, and the controller functions to compare the temperature of the smoke with the preset temperature threshold value, such that, when the temperature of the smoke is lower than the preset temperature threshold value, the controller instructs the power source to increase power output to the atomizer, and/or when the temperature of the smoke is higher than or equal to the preset temperature threshold value, the controller instructs the power source to reduce power output to the atomizer.

Furthermore, when the sensor is a humidity sensor, the storage is reserved with, as a preset threshold value, a preset humidity threshold value, and the controller functions to compare the humidity of the smoke with the preset humidity threshold value, such that, when the humidity of the smoke is lower than or equal to the preset humidity threshold value, the controller instructs the power source to reduce power output to the atomizer, and/or when the humidity of the smoke is higher than the preset humidity threshold value, the controller instructs the power source to increase power output to the atomizer.

Furthermore, the battery device also includes a user input module that is in signal connection with the storage and functions to facilitate the input of a temperature threshold value or a humidity threshold value desired by a user.

A method for controlling an electronic cigarette that includes a mouthpiece, an atomizer and a battery device, where the mouthpiece includes a sensor, the battery device includes a controller, a storage and a power source, the sensor being a temperature sensor, and the control method includes the following steps: detecting, by the temperature sensor, a temperature of smoke, and providing feedback about the detected temperature of the smoke to the controller; comparing, by the controller, the temperature of the smoke with a preset temperature threshold value and, when the temperature of the smoke is lower than the preset temperature threshold value, instructing, by the controller, the power source to increase power output to the atomizer or, when the temperature of the smoke is higher than or equal to the preset temperature threshold value, instructing, by the controller, the power source to reduce power output to the atomizer.

A method for controlling an electronic cigarette that includes a mouthpiece, an atomizer and a battery device, wherein the mouthpiece includes a sensor, the battery device includes a controller, a storage and a power source, the sensor being a humidity sensor, and the control method includes the following steps: detecting, by the humidity sensor, a humidity of smoke, and providing feedback about the detected humidity of the smoke to the controller; comparing, by the controller, the humidity of the smoke with a preset humidity threshold value and, when the humidity of the smoke is lower than or equal to the preset humidity threshold value, instructing, by the controller, the power source to increase power output to the atomizer or, when the humidity of the smoke is higher than the preset humidity threshold value, instructing, by the controller, the power source to reduce power output to the atomizer.

An electronic cigarette, functioning to carry out the aforementioned method for controlling an electronic cigarette.

The disclosure has the following beneficial effects:

a temperature sensor or a humidity sensor or a temperature and humidity sensor is provided in an inner cavity of a mouthpiece, enabling real time detection of the temperature and/or the humidity of the smoke, so that the temperature and/or the humidity of the smoke can be adjusted through a control unit. Therefore, the user may receive smoke at a more desirable temperature and/or humidity, meeting the need of the user for the taste of the smoke.

Figure 1:
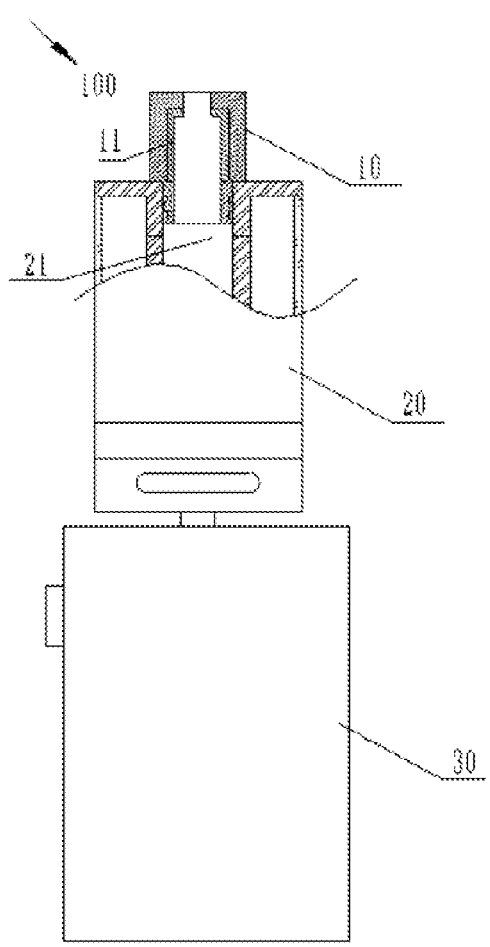
FIG. 1 is a semi-sectional view of an electronic cigarette according to a first embodiment of the present disclosure.

| | | | | |
|---|---|---|---|---|
| Electronic cigarette 100 | Mouthpiece 10 | Atomizer 20 | Battery device 30 | Sensor 11 |
| Smoke passage 21 | Controller 31 | Storage 32 | Power source 33 | User input sensor 34 |
| Electronic cigarette 200 | Mouthpiece 40 | Atomizer 50 | Battery device 60 | Sensor assembly 42 |
| Smoke passage 51 | Controller 61 | Storage 62 | Power source 63 | User input sensor 64 |
| Upper cover body 41 | Through hole 411 | Limiting portion 412 | Base 43 | Notch 431 |
| Limiting protrusion 432 | Accommodating groove 433 | Supporting plate 434 | Limiting groove 435 | Sealing ring 45 |
| Sensor 421 | Information transmission interface 422 | PCB board 423 | Protective sleeve 44 | Accommodating cavity 441 |
| Through hole 442 | Stepped groove 443 | Sliding groove 444 | Upper protrusion 445 | Lower protrusion 446 |
| | Air passage gap 46 | Sliding wing 424 | Groove 432 | |

DETAILED DESCRIPTION

For a clearer understanding of the technical features, objectives and effects of this disclosure, the specific implementation of this disclosure will now be described in detail with reference to the accompanying drawings. Apparently, the described embodiments are part of the embodiments of the present disclosure, rather than all of them. Any and all other embodiments obtained by those skilled in the art based on the presently disclosed embodiments without making any creative effort shall fall into the protection scope of the present disclosure.

First Embodiment

Referring to FIG. 1, the disclosure provides a mouthpiece 10, with at least one sensor 11 being provided in an inner cavity of the mouthpiece 10. The sensor 11 is a temperature or humidity sensor, functioning to detect the temperature or the humidity of the smoke.

It can be understood that, when the temperature of the smoke is higher, the atomization of the smoke liquid is more sufficient, i.e., the smoke is drier. When the temperature of the smoke is lower, the atomization of the smoke liquid is less sufficient, i.e., the smoke is wetter. Therefore, only one of the temperature and the humidity of the smoke needs to be detected.

Preferably, in order to detect the temperature or the humidity of the smoke more accurately, the sensors 11 are provided alternatively or symmetrically on both sides of the inner cavity of the mouthpiece 10, or the sensor 11 is provided in a circular form, and is circularly provided in the inner cavity of the mouthpiece 10, or the sensor 11 is provided along, or vertical to, or oblique to, an axial direction of the inner cavity of the mouthpiece 10.

In this embodiment, two sensors 11 are provided in the inner cavity of the mouthpiece 10, the two sensors 11 are symmetrically provided relative to the central axis of the mouthpiece 10, so that the temperature or the humidity of the smoke can be more accurately detected.

The disclosure also provides an atomizer 20 that is provided at one end with an aforementioned mouthpiece 10. A smoke passage 21 is provided in the atomizer 20, the smoke passage 21 is in communication with the inner cavity of the mouthpiece 10.

It can be understood that, in other embodiments, the at least one sensor 11 is provided in the smoke passage 21, or in the inner cavity of the mouthpiece 10 and the smoke passage 21.

The disclosure also provides an electronic cigarette 100 that includes the mouthpiece 10 and the atomizer 20, as well as a battery device 30. The battery device 30 is provided at an end of the atomizer 20 away from the mouthpiece 10.

Figure 2:
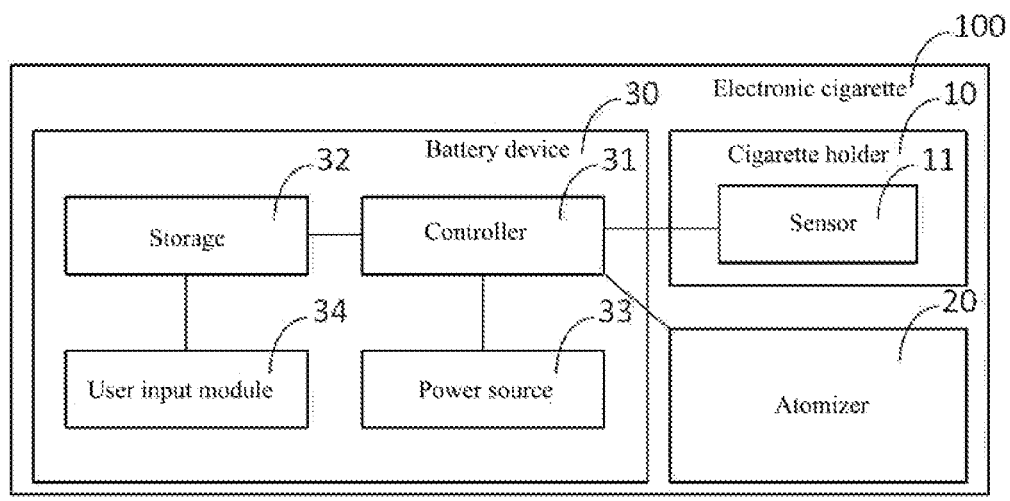
FIG. 2 is a structural block diagram of the electronic cigarette shown in FIG. 1.

Referring further to FIG. 2, the battery device 30 includes a controller 31, a storage 32 and a power source 33. The atomizer 20, storage 32 and power source 33 are electrically connected with the controller 31, and the sensor 11 is in signal connection with the controller 31.

The sensor 11 functions to detect the temperature or humidity of the smoke, and provide feedback about the detected temperature or humidity of the smoke to the controller 31.

The controller 31 functions to compare the temperature or the humidity of the smoke with a preset threshold value, and adjust the power output to the atomizer 20 from the power source 33 according to the comparison result. When the sensor 11 provides feedback about the temperature of the smoke, the controller 31 functions to compare the temperature of the smoke with the preset temperature threshold value, such that, when the temperature of the smoke is lower than the preset temperature threshold value, the controller 31 instructs the power source 33 to increase power output to the atomizer 20, and/or when the temperature of the smoke is higher than or equal to the preset temperature threshold value, the controller 31 instructs the power source 33 to reduce power output to the atomizer 20. When the sensor 11 provides feedback about the humidity of the smoke, the controller 31 functions to compare the humidity of the smoke with the preset humidity threshold value, such that, when the humidity of the smoke is lower than or equal to the preset humidity threshold value, the controller 31 instructs the power source 33 to reduce power output to the atomizer 20, and/or when the humidity of the smoke is higher than the preset humidity threshold value, the controller 31 instructs the power source 33 to increase power output to the atomizer 20.

The storage 32 functions to store the preset threshold value, and when the sensor 11 is a temperature sensor, the storage 32 functions to store a preset temperature threshold value, and/or when the sensor 11 is a humidity sensor, the storage 32 functions to store a preset humidity threshold value.

The power source 33 functions to supply power to the electronic cigarette 100.

Furthermore, the battery device 30 also includes a user input module 34. The user input module 34 is in signal connection with the storage 32, and functions to enable the setting of the preset temperature threshold value or humidity threshold value by a user.

The disclosure also provides a control method for the electronic cigarette 100.

Figure 3:
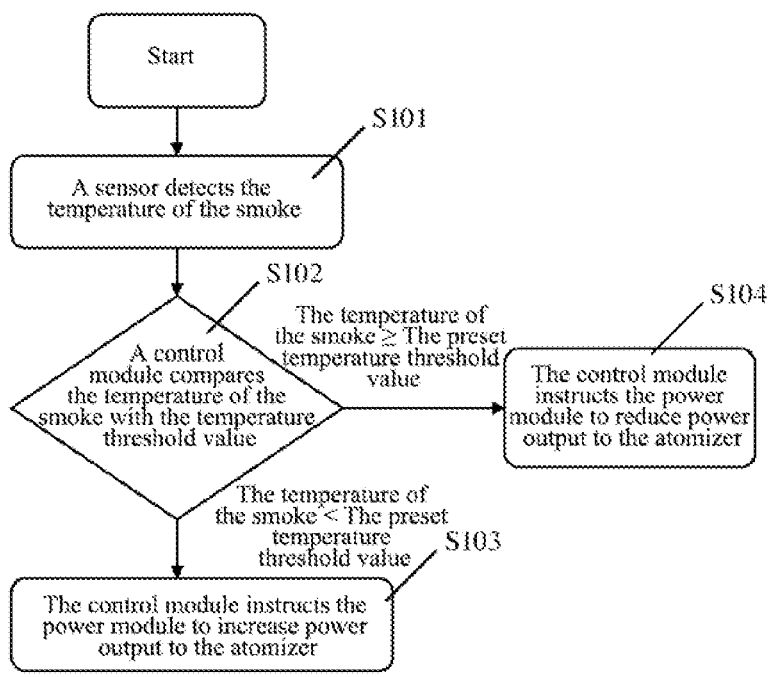
FIG. 3 is a flow chart of a control method for the electronic cigarette shown in FIG. 2.

Referring to FIG. 3, when the sensor 11 is a temperature sensor, the control method includes the following steps:

Step S101: the sensor 11 detects the temperature of the smoke, and provides feedback about the detected temperature of the smoke to the controller 31, and then goes to step S102;

Step S102: the controller 31 compares the temperature of the smoke with the preset temperature threshold value and, when the temperature of the smoke is lower than the preset temperature threshold value, proceed to step S103, and/or when the temperature of the smoke is higher than or equal to the preset temperature threshold value, proceed to step S104;

Step S103: the controller 31 instructs the power source 33 to increase power output to the atomizer 20; and Step S104: the controller 31 instructs the power source 33 to reduce power output to the atomizer 20.

Figure 4:
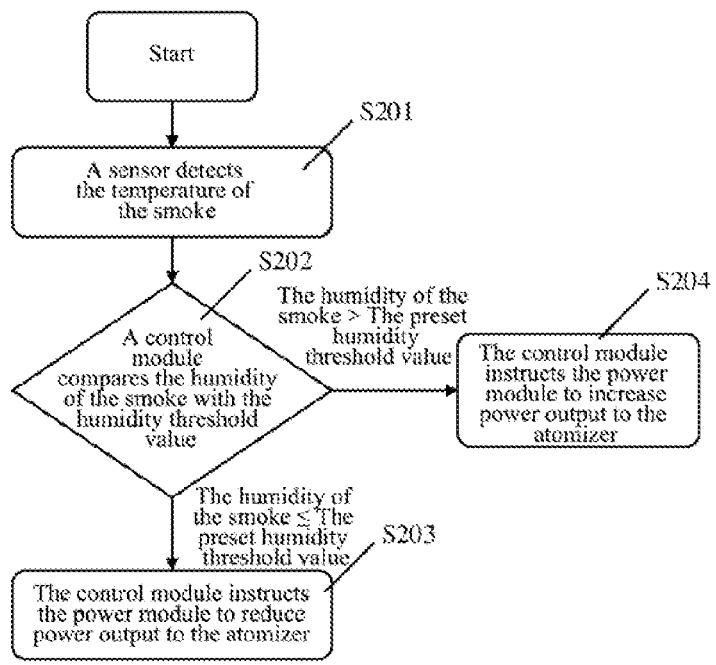
FIG. 4 is a flow chart of another control method for the electronic cigarette shown in FIG. 2.

Referring to FIG. 4, when the sensor 11 is a humidity sensor, the control method includes the following steps:

Step S201: the sensor 11 detects the humidity of the smoke, and provides feedback about the detected humidity of the smoke to the controller 31, and then goes to step S202;

Step S202: the controller 31 compares the humidity of the smoke with the preset humidity threshold value and, when the humidity of the smoke is lower than or equal to the preset humidity threshold value, proceed to step S203, and/or when the temperature of the smoke is higher than the preset humidity threshold value, proceed to step S204;

Step S203: the controller 31 instructs the power source 33 to reduce power output to the atomizer 20; and Step S204: the controller 31 instructs the power source 33 to increase power output to the atomizer 20.

Second Embodiment

Figure 5:
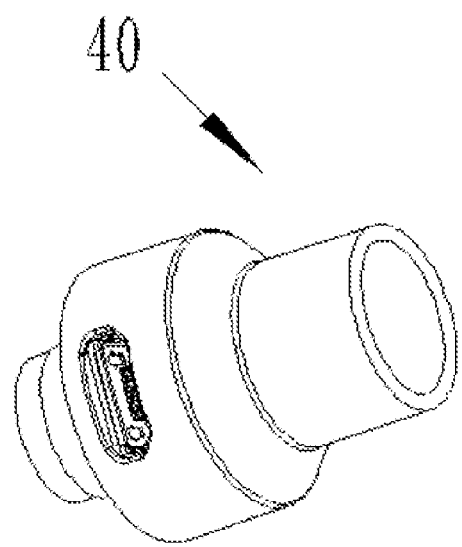
FIG. 5 is a perspective view of a mouthpiece according to a second embodiment of the present disclosure.
Figure 6:
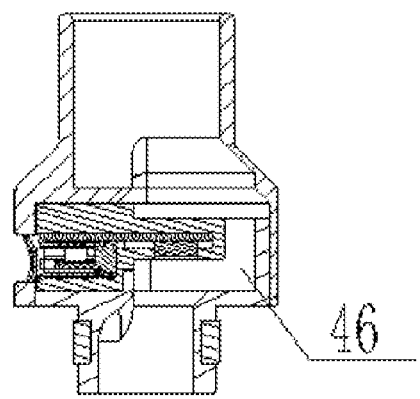
FIG. 6 is a cross-sectional view of the mouthpiece shown in FIG. 5.
Figure 7:
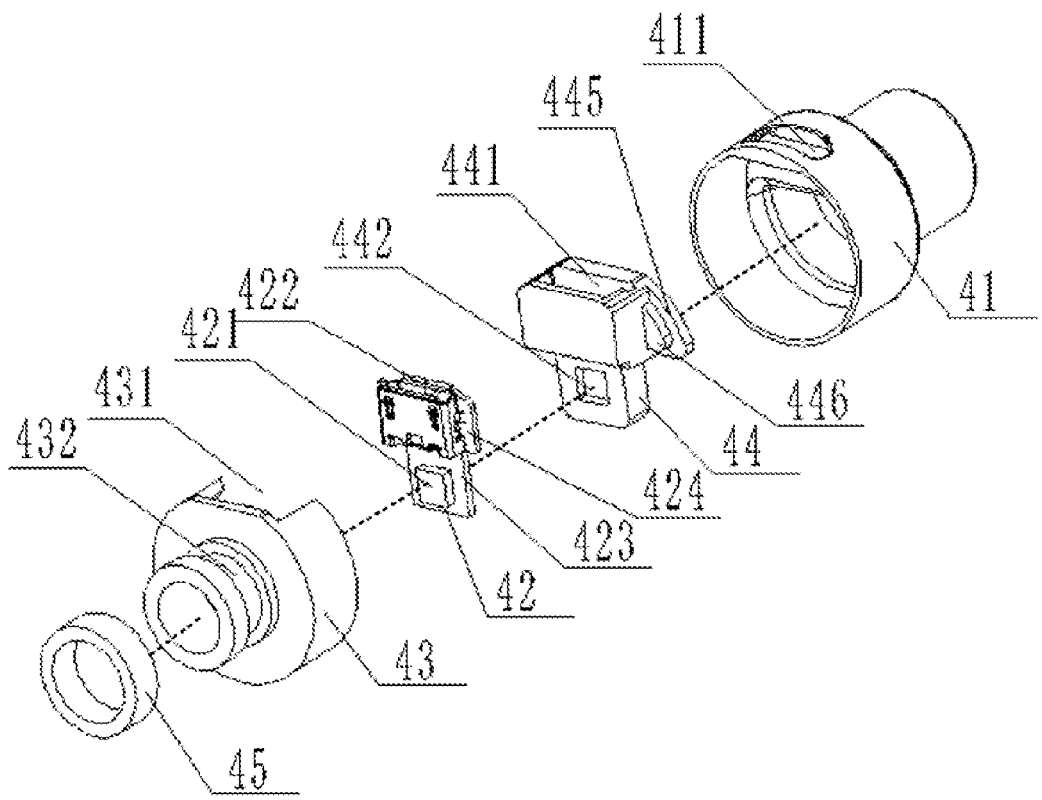
FIG. 7 is an exploded view of the mouthpiece shown in FIG. 5.

Referring to FIGS. 5, 6 and 7, the disclosure also provides another mouthpiece 40 that includes an upper cover body 41, a sensor assembly 42 and a base 43. The upper cover body 41 and the base 43 are both hollow structures which open at both ends. The upper cover body 41 is sleeved on one end of the base 43, and the inner surface of the upper cover body 41 and the inner surface of the base 43 jointly define an inner cavity of the mouthpiece 40. The sensor assembly 42 is fixed in the inner cavity of the mouthpiece 40, and an air passage gap 46 is formed in the inner cavity of the mouthpiece 40, so that the smoke flows from the bottom end of the base 43 into the air passage gap 46, and then out of the top end of the upper cover body 41. The sensor assembly 42 includes at least one sensor 421. The sensor 421 may be a temperature sensor or a humidity sensor or a temperature and humidity sensor, functioning to detect the temperature and/or the humidity of the smoke flowing through the air passage gap 46.

Preferably, the humidity-sensing assembly in the humidity sensor or the temperature and humidity sensor is of an electrolyte type, a ceramic type, a polymer type or a single-crystal semiconductor type.

Preferably, in order to detect the temperature and/or the humidity of the smoke more accurately, the sensors 421 are provided alternatively or symmetrically on both sides of the inner cavity of the mouthpiece 40, or the sensor 421 is in a circular form, and is circularly provided in the inner cavity of the mouthpiece 40, or the sensor 421 is provided along, or vertical to, or oblique to, an axial direction of the inner cavity of the mouthpiece 40.

Furthermore, the mouthpiece 40 also includes: a protective sleeve 44 that is provided with an accommodating cavity 441, where the sensor assembly 42 is detachably accommodated in the accommodating cavity 441, and is fixed in the inner cavity of the mouthpiece 40 together with the protective sleeve 44. The air passage gap 46 is a gap between the protective sleeve 44 and the inner cavity of the mouthpiece 40. The protective sleeve 44 is also provided with a through hole 442 that connects the accommodating cavity 441 with the air passage gap. The sensor 421 is provided in the through hole 442, so as to perform detection on the smoke flowing through the air passage gap 46.

Preferably, the protective sleeve 44 is made of rubber or silica gel.

Preferably, the shape of the through hole 442 is adapted to that of the sensor 421, such that the sensor 421 may be tightly fitted therein, preventing unwanted instability.

Furthermore, the protective sleeve 44 is provided along a radial direction of the mouthpiece 40; the accommodating cavity 441 is provided along an axial direction of the protective sleeve 44 and extends through the protective sleeve 44, until forming an open end for the accommodating cavity 441 on an end wall of the protective sleeve. The sensor assembly 42 also includes a PCB 423 that is provided on one end with the sensor 421, and on the other end with an information transmission interface 422. The shape of the PCB 423 is adapted to that of the accommodating cavity 441. The PCB board 423 is accommodated in the accommodating cavity 441 along an axial direction of the accommodating cavity 441. The information transmitting interface 422 is located at the open end of the accommodating cavity 441. The upper cover body 41 is provided with a through hole 4111 at a position corresponding to the open end of the accommodating cavity 441. Thus, an external information transmission device may be connected to the information transmission interface 422 through the through hole 411 and the open end of the accommodating cavity 441, facilitating information transmission between the sensor assembly 42 and the external environment.

Preferably, the dimension of the through hole 411 is adapted to that of the open end of the accommodating cavity 441, and the open end of the accommodating cavity 441 fits tightly with the through hole 411, so as to prevent the smoke from leaking into the gap between the open end of the accommodating cavity 441 and the through hole 411 and out of the through hole 411, causing smoke loss.

Preferably, the information transmission interface 422 is a USB interface.

Figure 8:
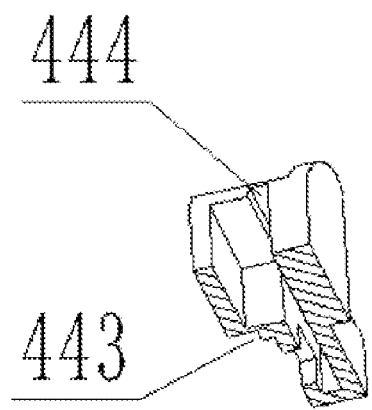
FIG. 8 is a cross-sectional view of the protective sleeve shown in FIG. 7.

Referring further to FIG. 8, a cavity wall of the accommodating cavity 441 is symmetrically provided with two sliding grooves 444 along an axial direction of the accommodating cavity 441; and two edges of the PCB 423 are provided with two sliding wings 424 engaged with the two sliding grooves 444, such that, when the PCB 423 is accommodated in the accommodating cavity 441 along the axial direction of the accommodating cavity 441, the sliding wings 424 are fitted into the corresponding sliding grooves 444, enabling effective fixing of the PCB board 423.

Figure 9:
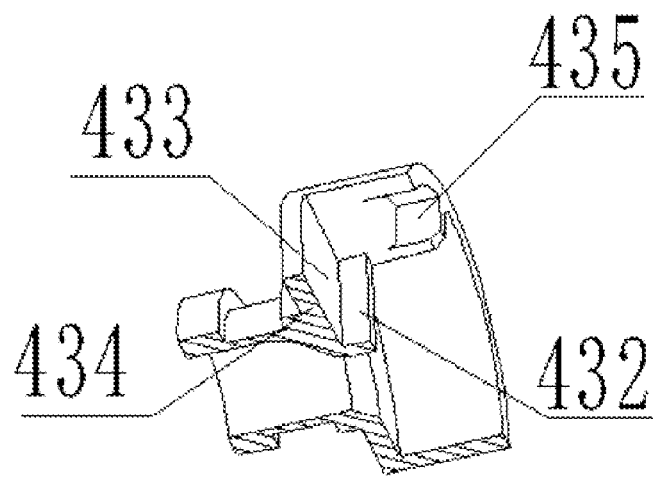
FIG. 9 is a cross-sectional view of the base shown in FIG. 7.

Referring further to FIG. 9, one side of the base 43 is depressed downward from its top, forming a notch 431 in communication with the through hole 411. A bottom edge of the notch 431 extends towards the inner cavity of the base 43, forming a supporting plate 434. In order to prevent the supporting plate 434 from blocking the circulation of smoke, a gap is left between the supporting plate 434 and an inner wall of another side of the base 43. An end of the supporting plate 434, which is away from the notch 431, extends upwards, forming a limiting protrusion 432. The notch 431, the inner wall of the base 43, the supporting plate 434 and the limiting protrusion 432 jointly define an accommodating groove 433. The protective sleeve 44 is at least partially accommodated in the accommodating groove 433, and the open end of the accommodating cavity 441 faces the notch 431. The limiting protrusion 432 can limit the radial movement of the protective sleeve 44 along the mouthpiece 40.

Furthermore, the protective sleeve 44 is provided on its bottom, at a position corresponding to the limiting protrusion 432, with a stepped groove 443 that abuts against the limiting protrusion 432, effectively preventing the protective sleeve 44 from moving along the radial direction of the inner cavity of the mouthpiece 40.

Furthermore, the inner wall of the base 43 is provided with a limiting groove 435 at positions close to both ends of the notch 431, respectively; and both sides of the protective sleeve 44 are respectively provided with a lower protrusion 446 at positions corresponding to the limiting grooves 435, where the lower protrusions 446 fits tightly into the corresponding limiting grooves 435, reliably fixing the protective sleeve 44.

Figure 10:
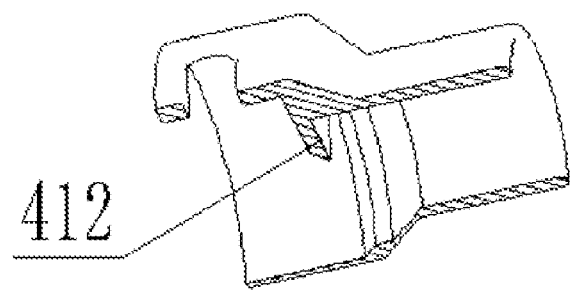
FIG. 10 is a cross-sectional view of the upper cover shown in FIG. 7.

Referring further to FIG. 10, the upper cover body 41 is provided on an inner wall of one side with a limiting portion 412 that extends along the radial direction of the upper cover body 41 and is above the through hole 411. In order to prevent the limiting portion 412 from blocking the circulation of the smoke, a gap is left between the limiting portion 412 and an inner wall of another side of the upper cover body 41. An upper surface of the lower protrusion 446 is provided with an upper protrusion 445 at a position corresponding to the limiting portion 412, the upper protrusion 445 being provided between the limiting portion 412 and the top end of the base 43, effectively limiting the axial movement of the protective sleeve 44 along the mouthpiece 40.

Furthermore, the base 43 is provided around a periphery of one end opposite to the upper cover body 41 with a groove 432 along a circumferential direction of the base 43, and a sealing ring 45 is provided in the groove 432. The sealing ring 45 enables a more reliable engagement between the mouthpiece 40 and the atomizer 50, while effectively preventing the smoke from leaking out of the contacting position between the mouthpiece 40 and the atomizer 50.

Figure 11:
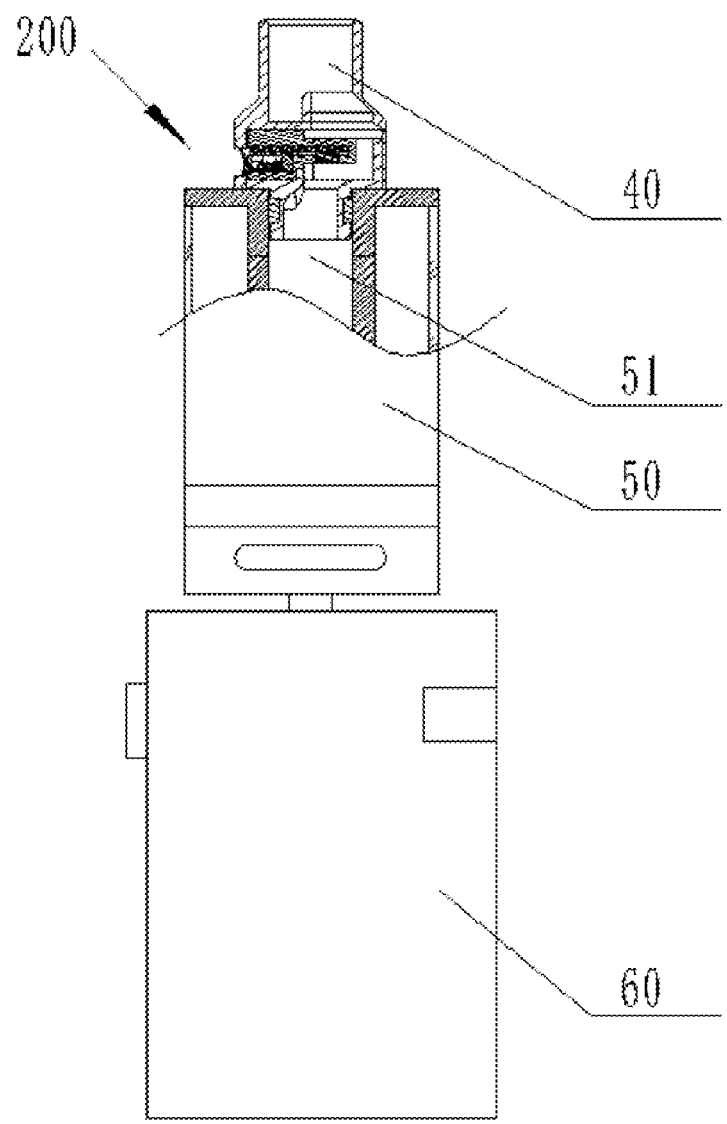
FIG. 11 is a semi-sectional view of the electronic cigarette in the second embodiment.

Referring to FIG. 11, the disclosure also provides an atomizer 50 that is provided at one end with an aforementioned mouthpiece 40. In this embodiment, the atomizer 50 is connected to an end of the base 43 away from the upper cover body 41. A smoke passage 51 is provided in the atomizer 50, the smoke passage 51 is in communication with the inner cavity of the mouthpiece 40.

The disclosure also provides an electronic cigarette 200 that includes the mouthpiece 40 and the atomizer 50, as well as a battery device 60. The battery device 60 is provided at an end of the atomizer 50 away from the mouthpiece 40.

When the sensor 421 is a temperature sensor or a humidity sensor, the battery device 60 includes a controller 61, a storage 62 and a power source 63. The atomizer 50, storage 62 and power source 63 are electrically connected with the controller 61, and the sensor 421 is in signal connection with the controller 61. The functions of, and cooperation between, the sensor 421 and the battery device 60 are the same as those for the sensor 11 and the battery device 30 in the first embodiment, which will not be repeated herein.

Figure 12:
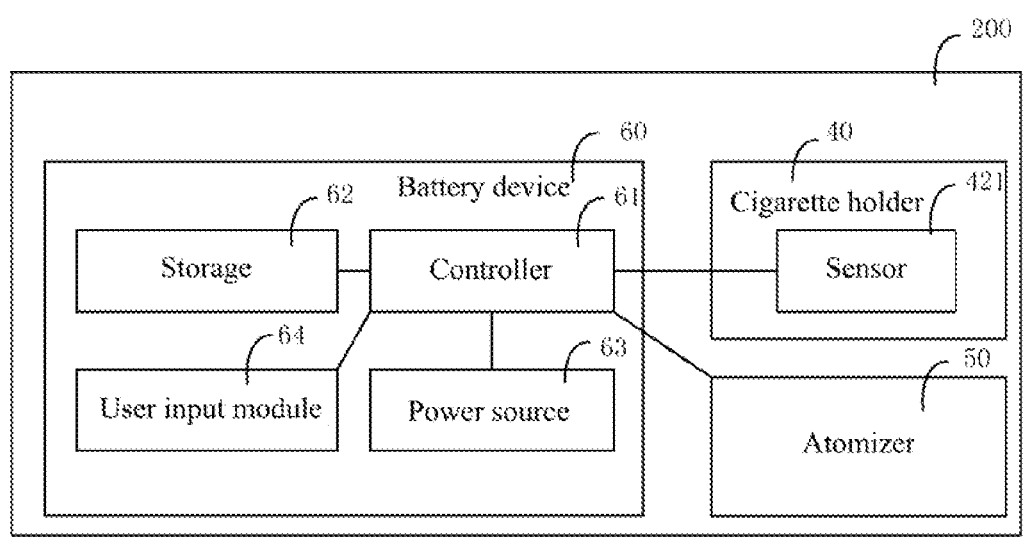
FIG. 12 is a structural block diagram of the electronic cigarette shown in FIG. 11.

Referring to FIG. 12, when the sensor 421 is a temperature and humidity sensor, the battery device 60 includes a controller 61, a storage 62, a power source 63 and a user input module 64. The atomizer 50, storage 62, power source 63 and user input module 64 are all electrically connected with the controller 61, and the sensor 421 is in signal connection with the controller 61.

The sensor 421 functions to detect the temperature and humidity of the smoke, and provide feedback about the detected temperature and humidity of the smoke to the controller 61.

The user input module 64 enables a user to select a reference quantity and returns the selected reference quantity to the controller 61, the reference quantity being the temperature or the humidity of the smoke.

According to the reference quantity selected by the user, the controller 61 functions to compare the temperature or the humidity of the smoke with a corresponding preset threshold value, and adjust the power output to the atomizer 50 from the power source 63 according to the comparison result. When the reference quantity selected by the user is the temperature of the smoke, the controller 61 functions to compare the temperature of the smoke with the preset temperature threshold value, such that, when the temperature of the smoke is lower than the preset temperature threshold value, the controller 61 instructs the power source 63 to increase power output to the atomizer 50, and/or when the temperature of the smoke is higher than or equal to the preset temperature threshold value, the controller 61 instructs the power source 63 to reduce power output to the atomizer 50. When the reference quantity selected by the user is the humidity of the smoke, the controller 61 functions to compare the humidity of the smoke with the preset humidity threshold value, such that, when the humidity of the smoke is lower than or equal to the preset humidity threshold value, the controller 61 instructs the power source 63 to reduce power output to the atomizer 50, and/or when the humidity of the smoke is higher than the preset humidity threshold value, the controller 61 instructs the power source 63 to increase power output to the atomizer 50.

The storage 62 functions to store the preset threshold value, including a preset temperature threshold value and a preset humidity threshold value.

The power source 63 functions to supply power to the electronic cigarette 200.

It can be understood that a user may be sensitive to the temperature as well as the humidity. The sensor 421 is a temperature and humidity sensor, and a user may select a reference quantity through the user input module 64, thereby improving user experience.

The disclosure also provides a control method for the electronic cigarette 200.

When the sensor 421 is a temperature sensor or a humidity sensor, the control method is the same as the control method in the first embodiment, which will not be repeated herein.

Figure 13:
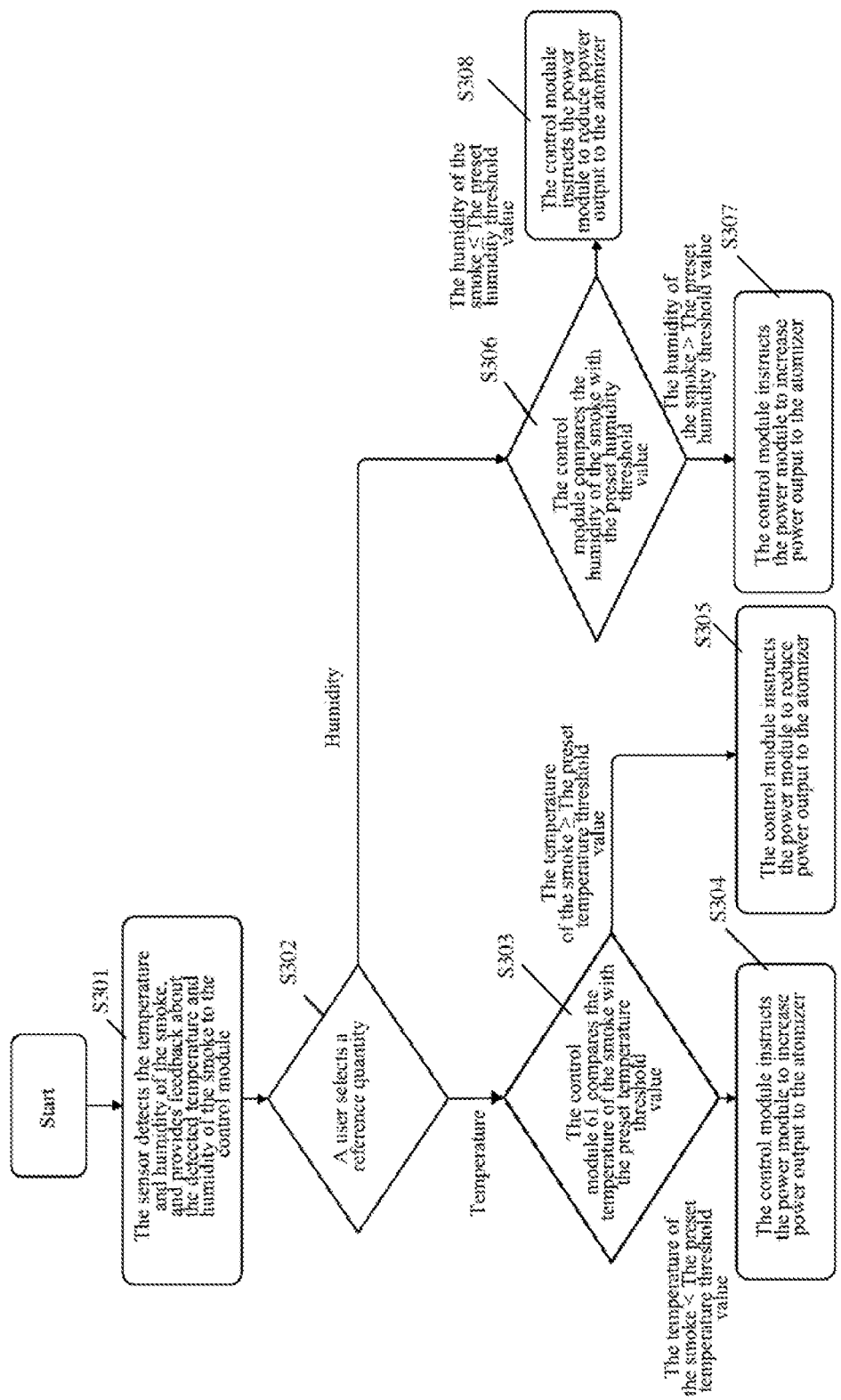
FIG. 13 is a flow chart of a control method of the electronic cigarette shown in FIG. 12.

Referring to FIG. 13, when the sensor 421 is a temperature and humidity sensor, the control method includes the following steps:

Step S301: the sensor 421 detects the temperature and humidity of the smoke, and provides feedback about the detected temperature and humidity of the smoke to the controller 61, and then proceed to step S302;

Step S302: a user selects a reference quantity, and when the user selects the temperature as the reference quantity, proceed to step S303, and when the user selects the humidity as the reference quantity, proceed to step S306;

Step S303: the controller 61 compares the temperature of the smoke with the preset temperature threshold value and, when the temperature of the smoke is lower than the preset temperature threshold value, proceed to step S304, and/or when the temperature of the smoke is higher than or equal to the preset temperature threshold value, proceed to step S305;

Step S304: the controller 61 instructs the power source 63 to increase power output to the atomizer 50.

Step S303: the controller 61 instructs the power source 63 to reduce power output to the atomizer 50.

Step S306: the controller 61 compares the humidity of the smoke with the preset humidity threshold value and, when the humidity of the smoke is higher than the preset humidity threshold value, proceed to step S307, and/or when the temperature of the smoke is lower than or equal to the preset humidity threshold value, proceed to step S308;

Step S307: the controller 61 instructs the power source 63 to increase power output to the atomizer 50.

Step S308: the controller 61 instructs the power source 63 to reduce power output to the atomizer 50.

The disclosure has the following beneficial effects:

a temperature sensor or a humidity sensor or a temperature and humidity sensor is provided in an inner cavity of the mouthpiece 10/40, enabling real time detection of the temperature and/or humidity of the smoke, as well as comparison of the detected temperature or humidity with a preset threshold value, so as to control the power output from the power source 33/63 to the atomizer 20/50 according to the comparison result. Therefore, the user may receive smoke at a more desirable temperature and/or humidity, meeting the need of the user for the taste of the smoke.

What is claimed is:

1. A mouthpiece, comprising:
   an upper cover body;
   a sensor assembly;
   a base, wherein:
      both of the upper cover body and the base are hollow structures which open at both ends;
      the upper cover body is sleeved on one end of the base;
      an inner surface of the upper cover body and an inner surface of the base jointly define an inner cavity of the mouthpiece;
      the sensor assembly is fixed in the inner cavity of the mouthpiece;
      an air passage gap is formed in the inner cavity of the mouthpiece; and
      the sensor assembly comprises at least one sensor that is a temperature sensor or a humidity sensor or a temperature and humidity sensor, which functions to detect a temperature and/or a humidity of e-cigarette vapor flowing through the air passage gap; and
   a protective sleeve that is provided with an accommodating cavity, wherein:
      the sensor assembly is detachably accommodated in the accommodating cavity, and the sensor assembly is fixed in the inner cavity of the mouthpiece together with the protective sleeve; and
      the protective sleeve is provided along a radial direction of the mouthpiece;
      the accommodating cavity opens along an axial direction of the protective sleeve and extends through the protective sleeve, until forming an open end for the accommodating cavity on an end wall of the protective sleeve;
      the sensor assembly further comprises a printed circuit board (PCB) that is provided on one end with the sensor, and on the other end with an information transmission interface, wherein the PCB is accommodated in the accommodating cavity and extends along an axial direction of the accommodating cavity, and the information transmission interface is located at the open end of the accommodating cavity; and
      the upper cover body is provided with a second through hole at a position corresponding to the open end of the accommodating cavity.

2. The mouthpiece according to claim 1, wherein:
   the air passage gap is between the protective sleeve and the inner cavity of the mouthpiece;
   a first through hole connecting the accommodating cavity with the air passage gap is defined in the protective sleeve; and
   the at least one sensor is provided in the first through hole.

3. The mouthpiece according to claim 1, wherein:
   a first side of the base is depressed downward from its top, forming a notch in communication with the second through hole;
   a bottom edge of the notch extends towards the inner cavity of the base, forming a supporting plate;
   a gap is left between the supporting plate and an inner wall of a second side of the base to allow for circulation of e-cigarette vapor;
   a limiting protrusion that extends upward is formed at an end of the supporting plate away from the notch;
   wherein the notch, the inner wall of the base, the supporting plate and the limiting protrusion jointly define an accommodating groove, and the protective sleeve is at least partially accommodated in the accommodating groove; and
   the open end of the accommodating cavity faces the notch.

4. The mouthpiece according to claim 3, wherein:
   the protective sleeve is provided with a stepped groove that abuts against the limiting protrusion for preventing the protective sleeve from moving along a radial direction of the inner cavity of the mouthpiece;
   the inner wall of the base is provided with a limiting groove close to both ends of the notch, respectively; and
   both sides of the protective sleeve are provided with a lower protrusion at positions corresponding to the limiting grooves, wherein the lower protrusion fits into the limiting groove for fixing the protective sleeve.

5. The mouthpiece according to claim 1, wherein:
   a cavity wall of the accommodating cavity is symmetrically provided with two sliding grooves along an axial direction of the accommodating cavity; and
   each of two edges of the PCB is provided with a sliding wing to engage with one of the two sliding grooves, such that, when the PCB is accommodated in the accommodating cavity along the axial direction of the accommodating cavity, the sliding wings are fitted into the two sliding grooves.

6. The mouthpiece according to claim 1, wherein the information transmission interface is a USB interface.

7. The mouthpiece according to claim 4, wherein:
   the upper cover body is provided on an inner wall of a third side with a limiting portion that extends along the radial direction of the upper cover body and is above the second through hole;
   a gap is left between the limiting portion and the inner wall of a fourth side of the upper cover body to allow for circulation of e-cigarette vapor; and an upper surface of the lower protrusion is provided with an upper protrusion at a position corresponding to the limiting portion, the upper protrusion being provided between the limiting portion and the top end of the base.

8. The mouthpiece according to claim 1, wherein the protective sleeve is made of rubber or silica gel.

9. The mouthpiece according to claim 1, wherein the base is provided around a periphery of one end opposite to the upper cover body with a groove along a circumferential direction of the base, and a sealing ring is provided in the groove.

10. A mouthpiece, comprising:
- at least one sensor in an inner cavity of the mouthpiece, wherein one of the at least one sensor is a temperature or humidity sensor that functions to detect a temperature or a humidity of e-cigarette vapor, and
- a protective sleeve provided with an accommodating cavity, wherein the at least one sensor is detachably accommodated in the accommodating cavity, and the at least one sensor is fixed in the inner cavity of the mouthpiece together with the protective sleeve; and
- the protective sleeve is provided along a radial direction of the mouthpiece;
- the accommodating cavity opens along an axial direction of the protective sleeve and extends through the protective sleeve, until forming an open end for the accommodating cavity on an end wall of the protective sleeve;
- the sensor assembly further comprises a printed circuit board (PCB) that is provided on one end with the sensor, and on the other end with an information transmission interface, wherein the PCB is accommodated in the accommodating cavity and extends along an axial direction of the accommodating cavity, and the information transmission interface is located at the open end of the accommodating cavity; and
- the upper cover body is provided with a second through hole at a position corresponding to the open end of the accommodating cavity.

11. The mouthpiece according to claim 10, wherein the at least one sensor is provided alternatively or symmetrically on both sides of the inner cavity of the mouthpiece, or the sensor is in a circular form, and is circularly provided in the inner cavity of the mouthpiece, or the at least one sensor is provided along, or vertical to, or oblique to, an axial direction of the inner cavity of the mouthpiece.

12. An atomizing device, comprising an atomizer, and a mouthpiece according to claim 10, wherein the mouthpiece is provided on one end of the atomizer.

13. The atomizing device according to claim 12, further comprising a battery device connected to another end of the atomizer which functions to power the atomizer, and the atomizing device further comprises a controller, a storage and a power source, wherein the atomizer, the storage and the power source are electrically connected with the controller, and the at least one sensor is in signal connection with the controller, wherein:
- the at least one sensor further functions to provide feedback about the detected temperature or humidity of the e-cigarette vapor to the controller; the controller functions to compare the temperature or the humidity of the e-cigarette vapor with a preset threshold value, and adjust a power output to the atomizer from the power source according to the comparison result;
- the storage functions to store the preset threshold value; and
- the power source functions to supply power to the atomizing device.

14. The atomizing device according to claim 13, wherein:
when the at least one sensor is a temperature sensor, the storage is reserved with a preset temperature threshold value, and the controller functions to compare the temperature of the e-cigarette vapor with the preset temperature threshold value, such that:
- when the temperature of the e-cigarette vapor is lower than the preset temperature threshold value, the controller instructs the power source to increase power output to the atomizer; and/or
- when the temperature of the e-cigarette vapor is higher than or equal to the preset temperature threshold value, the controller instructs the power source to reduce power output to the atomizer.

15. The atomizing device according to claim 13, wherein:
when the at least one sensor is a humidity sensor, the storage is reserved with a preset humidity threshold value, and the controller functions to compare the humidity of the e-cigarette vapor with the preset humidity threshold value, such that:
- when the humidity of the e-cigarette vapor is lower than or equal to the preset humidity threshold value, the controller instructs the power source to reduce power output to the atomizer; and/or
- when the humidity of the e-cigarette vapor is higher than the preset humidity threshold value, the controller instructs the power source to increase power output to the atomizer.

* * * * *